United States Patent [19]

Loiterman

[11] Patent Number: 4,983,165

[45] Date of Patent: Jan. 8, 1991

[54] GUIDANCE SYSTEM FOR VASCULAR CATHETER OR THE LIKE

[76] Inventor: David A. Loiterman, 1806 Midwest Club, Oak Brook, Ill. 60521

[21] Appl. No.: 469,159

[22] Filed: Jan. 23, 1990

[51] Int. Cl.$^5$ .............................................. A61M 25/10
[52] U.S. Cl. ...................... 604/95; 604/101; 604/164
[58] Field of Search ............ 604/101, 95, 96, 99, 604/164, 264, 280; 606/194

[56] References Cited

U.S. PATENT DOCUMENTS 4,066,070  1/1978  Utsugi ................................. 604/95
4,934,786  6/1990  Krauter ............................... 604/95

Primary Examiner—Stephen C. Pellegrino
Attorney, Agent, or Firm—Allegretti & Witcoff, Ltd.

[57] ABSTRACT

A catheter for introduction into the vascular system of an animal is disclosed comprising: a tubular member with a proximal and distal end and an inner and outer surface, the outer surface provided with an inflatable steering means, the inner surface defining a passage, the passage provided with a guide wire; and a control means operably linked to the inflatable steering means for selectively inflating same, said control means inflating said inflatable steering means to align said tubular member toward a selected branch of the vascular system, said guide wire being directed through the passage into said selected branch of said vascular system and said tubular member being advanced over the guide wire into said selected branch of the vascular system.

18 Claims, 1 Drawing Sheet

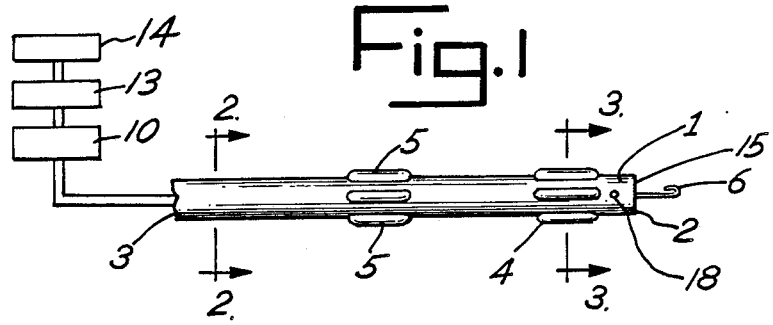
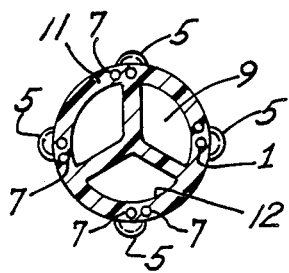
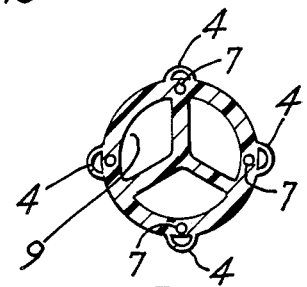
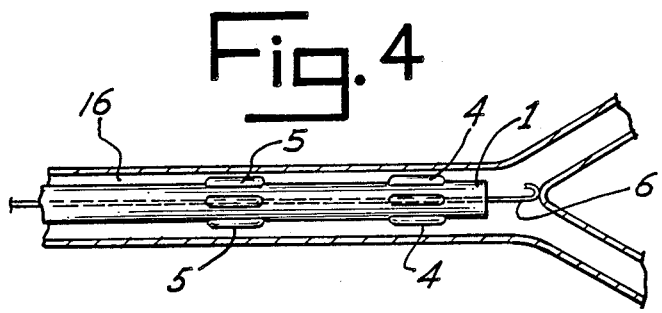
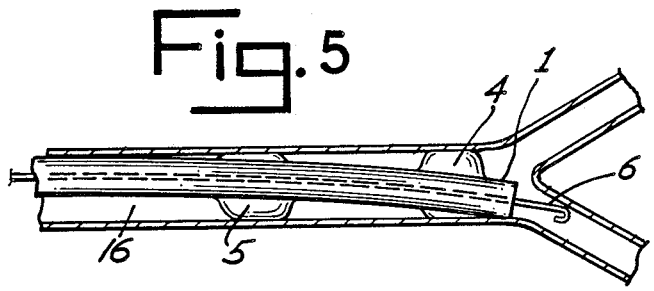
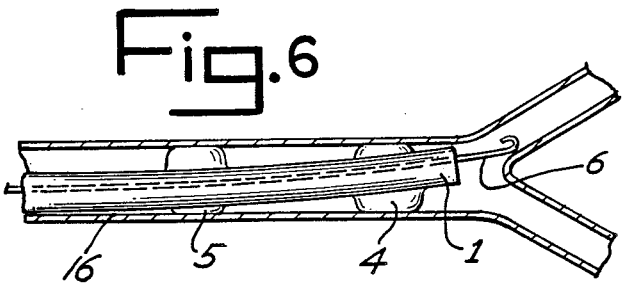

GUIDANCE SYSTEM FOR VASCULAR CATHETER OR THE LIKE

BACKGROUND OF THE INVENTION

1. Field of the Invention

The present application relates to catheters, cannulae, endoscopes, and fiberoptic delivery systems of various forms of light, including laser, and particularly to a guidance system for directing such devices through the vascular system from a position external to the body.

2. Description of the Background Art

Many commerically available catheters and endoscopes exist for introducing into the vasuclar system a variety of surgical tools and materials, such as radiographic contrast materials, angioplasty baloons, fiberoptic cameras and lights, laser light, and a wide array of cutting instruments. These catheters and endoscopes are constructed to have good torque and rotational control in addition to advance and withdraw capabilities.

However, these catheters and endoscopes lack the ability to negotiate a tortuous course, i.e., trackability or steerability. Such catheters and endoscopes lack the ability to control vertical and horizontal movement of the tip of the device. For convenience of description, the term catheter will be used hereinafter. To overcome this problem, a series of catheters having different tip shapes, sizes, and stiffness are introduced on a flexible guide wire in order to appropriately deflect the tip in the proper direction.

Other attempts have been made in the past to provide catheters having distal ends which, when inserted into a body, are manipulatable to advance the catheter through body cavities. Catheters have been developed to include permanent magnets and employ magnetic fields to bend the distal end of the catheter. However, these devices are quite difficult to control and manipulate. Other catheters include fluid conduits to expand the distal end, but not to guide the distal end of the catheter.

Some work has been done to produce catheters which are readily insertable while being effectively anchorable in a body cavity. For example, the distal end of a catheter may be formed into a desired shape by using a material exhibiting mechanical memory that is triggered by heat. By heating the mechanical memory material, the distal end of the catheter is shaped to anchor the catheter within the body. However, the change of the shape or other movement of the distal end in these prior devices is limited to a single direction. Once the memory material has been heated causing the distal end to move in said single direction to assume its characteristic anchoring shape, it becomes necessary to deform the distal end manually at a temperature below the transition temperature of the mechanical memory material in order to change the shape of the distal end. The need for manual manipulation of a catheter once it is inserted into a body limits the steerability and aimability of the catheter.

U.S. Pat. Nos. 4,543,090, 4,601,705, and 4,758,222, all to McCoy, teach a catheter including an elongated tubular member having a proximal end and a distal end for insertion into the body and a plurality of temperature-activated memory elements in the distal end of the tubular member. Each memory element assumes a first shape when heated to a predetermined temperature. Each memory element is coupled to at least one other memory element so that movement of one element results in movement of the other element. Each memory element is moved to a second shape when the memory element coupled thereto is heated to the predetermined temperature. A control system adjacent the proximal end of the tubular member allows an operator to selectively control the temperature of each temperature-activated element to deflect the distal end of the tubular member so as to direct the course of the tubular member toward an organ or tissue within the body. The control system includes a power supply source, electrical connections between the power supply source and the memory elements in the distal end of the tubular member, and a control device for selectively applying power to heat the memory elements to their predetermined temperatures to deflect the distal end of the tubular member so as to steer the tubular member or aim the distal end of the tubular member within the body.

U.S. Pat. No. 4,636,195 to Wolinsky teaches a catheter having distal and proximate balloon segments expansible to produce a chamber around arterial plaque and a conduit for delivering solubilizing liquid into the chamber. The catheter may also contain a central expansible balloon to assist in forcing the liquid into the plaque and to compress the plaque. Several solubilizing liquids are described.

Technology exists for manufacturing small catheters having multiple lumens or channels. In addition, technology exists for the delivery of fluids to small inflatable balloons located at the end of a catheter to achieve angioplasty.

Manufacturers of gastrointestinal fiberoptic endoscopes have developed extremely sophisticated mechanical means involving cables and wheels to achieve tip mobility in their endoscopes. To date, no one has been able to transfer this technology to a vascular catheter because of the catheter's inherently small size, the extreme flexibility required to negotiate the vascular system, and the extreme length required to reach the coronary arteries from peripheral location such as the femoral artery in the groin.

Thus, there is a need for an aimable and steerable guidance system for a vascular catheter that may be less than 1 mm in diameter, extremely flexible, and very long.

SUMMARY OF THE INVENTION

An object of the present invention is to provide a steerable catheter which may be less than 1 mm in diameter, extremely flexible, very long, easy to operate, and steerable in a plurality of different directions in the vascular system.

Another object of the present invention is to provide a steerable catheter which is easy to operate and aim at obsructions in the vascular system.

A further object of the present invention is to provide a steerable catheter having an inflatable steering means and a control means operatively linked to the inflatable steering means for selectively inflating same. The control means inflates the inflatable steering means to align the catheter in the vascular system. The catheter is then advanced over a guide wire slidably mounted in a passage in the catheter.

Further objects and advantages of the present invention will be made known in the following description of the preferred embodiments of the invention.

BRIEF DESCRIPTION OF THE DRAWINGS

The preferred embodiment of the present invention will be described in relation to the accompanying drawing, wherein like numerals in the various figures refer to like elements, and wherein:

FIG. 1 is a longitudinal view of the body of a steerable and aimable catheter;

FIG. 2 is a transverse cross-sectional view of the body of the steerable catheter taken generally along line 2—2 of FIG. 1;

FIG. 3 is a transverse cross-sectional view of the steerable catheter taken along line 3—3 of FIG. 1;

FIG. 4 is a longitudinal cross-sectional view through a section of a vascular system and the steerable catheter showing the aiming balloons uninflated;

FIG. 5 is a longitudinal cross-sectional view through a section of the vascular system and the steerable catheter showing the aiming balloons inflated to direct the catheter into a lower branch of the vascular system;

FIG. 6 is a longitudinal cross-sectional view through a sectional of the vascular system and the steerable catheter showing the aiming balloons inflated to direct the catheter into an upper branch of the vascular system.

DETAILED DESCRIPTION OF THE PREFERRED EMBODIMENTS

Referring to FIGS. 1, 2 and 3, the preferred apparatus comprises, in part, a tubular member 1 with a proximal end 3, a distal end 2, an outer surface 11, and an inner surface 12. The tubular member 1 is generally less than 1 mm in diameter, but may be a variety of sizes depending upon application. The tubular number 1 may be made of any suitable material, such as, for example, Teflon, plastic, cross-linked KYNAR TM or polyethylene. The distal end 2 of tubular member 1 ends in a catheter tip 15. The catheter tip 15 may be provided with a radio-opaque marker 18 for fluoroscopic imaging and the catheter tip 15 may be flat, rounded or tapered depending on the ultimate target site.

The inner surface 12 defines three working channels 9. One of the working channels 9 are provided with a slidably mounted guidewire 6. The working channels may also be provided with various wires, instruments, fiberoptic light bundles and flushing fluids for delivery to a desired portion of a vascular system.

The outer surface 11 is provided with a distal set of resilient aiming balloons 4 and a proximal set of resilient aiming balloons 5. The aiming balloons may be produced from any suitable material, for example, the same material, as the tubular member 1. As shown in FIG. 1, the distal set of aiming balloons 4 and the proximal set of aiming balloons 5 are both positioned at 0, 90, 180, and 270 degrees. In other words, the proximal set 5 is in direct alignment with the distal set.

The segment of tubular member 1 between the proximal set 5 and the distal set 4 of aiming balloons is stiffer and more rigid relative to the balance of the catheter which is supple. This difference in stiffness allows for more efficient deflection of the tip with differential balloon inflation.

The length of the segment between the distal set 4 and proximal set 5 is variable and related to the diameter of tubular member 1. Furthermore, the size of each balloon when inflated is related to the diameter of tubular member 1, the diameter of the portion of the vascular system that the distal end of the catheter is in, and the diameter of tubular member 1. Therefore, the size of an inflated balloon will be the greatest when the catheter is of a small diameter, the vascular system is of a large diameter and the inflated balloon is inflated to direct the catheter in a direction directly opposite from the balloon.

Each individual aiming balloon is operatively connected to a control tubule or duct 7 located between the inner and outer surface of the tubular member 1. The control ducts 7 are operatively connected to a servo pump 10. The servo pump 10 is operatively electrically connected to an electronic microprocessor based computer 13. The microprocessor based computer 13 is operatively electrically connected to a joy stick mechanism 14. The sets of aiming balloons 4 and 5, duct 7 and servo pump 10 are charged with a suitable fluid or gas for inflation of the sets of aiming balloons 4 and 5, such as, for example, isotonic saline.

After the catheter tip 15 is inserted into a vascular system 16 from a peripheral location such as the femoral artery in the groin, the catheter may be aimed in and steered through the vasuclar system 16. Referring now to FIGS. 4, 5 and 6, an operator controls the deflection of tip 15 with the joy stick 14. Movement of the joy stick 14 in a direction relative to that desired for catheter tip deflection causes the microprocessor computer 13 to selectively inflate individual aiming balloons by pumping the fluid or gas through the control ducts 7 into the aiming balloons such that the catheter tip 15 is deflected or aimed at the desired branch of the vascular system 16. Guide wire 6 is then slidably advanced into the desired branch of the vasular system and the catheter advanced over the guide wire 6 into that branch of the vascular system.

In an alternative embodiment of the invention, the joy stick mechanism is replaced with an ultrasound unit operatively electrically connected to a forward looking ultrasound crystal mounted on the catheter tip 15. The ultrasound unit would provide feed back control to the microprocessor computer to center the tip 15 in the branch of the vascular system.

The forward looking ultrasound crystal enables tip 15 to be centered toward a segment of the vascular system one to two millimeters in front of the tip 15. Laser energy could then be delivered from a laser provided in one of the working channels 9 to disintegrate blockages short distances in front of the tip 15.

In another embodiment of the present invention, the distal set of aiming balloons 4 is offset from the proximal set of aiming balloons 5 by an angle of about 45 degrees.

The invention, and the manner and process of making and using it, are now described in such full, clear, concise and exact terms as to enable any person skilled in the art to which it pertains, to make and use the same. It is to be understood, of course, that the foregoing describes a preferred embodiment of the present invention and that modifications may be made therein without departing from the spirit or scope of the present invention as set forth in the claims. As examples, the components of the preferred embodiment constitute one form of various means plus function elements in which the invention may be embodied. To particularly point out and distinctly claim the subject matter regarded as invention, the following claims conclude this specification.

What is claimed is:

1. A steerable catheter for introduction into the vascular system of an animal comprising: a tubular member with a proximal and distal end and an inner and outer surface, the outer surface provided with an inflatable steering means, the inner surface defining a passage, the passage provided with a guide wire; and a control means operably linked to the inflatable steering means for selectively inflating same, said control means inflating said inflatable steering means to align said tubular member toward a selected branch of the vascular system, said guide wire being directed through the passage into said selected branch of said vascular system and said tubular member being advanced over the guide wire into said selected branch of the vascular system.

2. A catheter according to claim 1, wherein the inflatable steering means is a plurality of aiming balloons on the outer surface of the tubular member connected to a plurality of control tubes located between the inner and outer surfaces of the tubular member.

3. A catheter according to claim 2, wherein the aiming balloons are positioned at the distal end of the tubular member.

4. A catheter according to claim 3, wherein the aiming balloons are arranged in two spaced groups.

5. A catheter according to claim 4, wherein the two spaced groups are positioned in direct alignment with each other.

6. A catheter according to claim 4, wherein the two spaced groups are offset from each other by an angle of about 45 degrees.

7. A catheter according to claim 4, wherein each of the two spaced groups include diametrically opposed balloons.

8. A catheter according to claim 7, wherein the passage further comprises a plurality of working channels.

9. A catheter according to claim 8, wherein the distal end of the tubular member further comprises a tip.

10. A catheter according to claim 9, wherein the tip further comprises a radio-opaque marker.

11. A catheter according to claim 10, wherein the control means is a servo pump operably attached to a microprocessor.

12. A catheter according to claim 11, wherein the control means further comprises a joy stick mechanism.

13. A catheter according to claim 12, wherein the working channels include instruments to remove blockages in the vascular system.

14. A catheter according to claim 12, wherein the working channels include fiberoptic light bundles for viewing the vascular system.

15. A catheter according to claim 9, wherein the tip further comprises an ultrasound crystal.

16. A catheter according to claim 15, wherein the ultrasound crystal is operably connected to an ultrasound unit, whereby the position of the catheter tip may be determined relative to a wall of the vascular system.

17. A method of steering a catheter comprising the steps of:
 (a) inserting a tubular member into a vascular system;
 (b) inflating an inflatable steering means provided on an outer surface of the tubular member having a proximal end and a distal end and an inner and an outer surface to deflect a catheter tip towards a desired direction in the vascular system;
 (c) directing a guide wire through a passage defined by the inner surface into the desired branch of the vascular system; and
 (d) advancing the tubular member over the guide wire into the desired branch of the vascular system.

18. A method according to claim 17, wherein the inflatable steering means is inflated by selectively pumping a fluid through a plurality of control tubes located between the inner and outer surfaces of the tubular members into a plurality of aiming balloons provided on the outer surfaces of the tubular member.

* * * * *